United States Patent [19]

Riexinger sen. et al.

[11] Patent Number: 4,536,929
[45] Date of Patent: Aug. 27, 1985

[54] DEVICE FOR MANUFACTURING A SHUTTER LINK FOR A MULTI-LINK OVERHEAD SHUTTER OR ROLLER BLIND

[75] Inventors: Gustav Riexinger sen., Brackenheim-Hausen; Rudolf Nagel, Schöneich, both of Fed. Rep. of Germany

[73] Assignee: Tuerenwerke Riexinger GmbH & Co. KG, Fed. Rep. of Germany

[21] Appl. No.: 522,454

[22] Filed: Aug. 11, 1983

Related U.S. Application Data

[62] Division of Ser. No. 308,552, Oct. 2, 1981, Pat. No. 4,470,444.

[30] Foreign Application Priority Data

Jul. 30, 1980 [WO] PCT Int'l Appl. .................. PCT/EP80/00066

[51] Int. Cl.³ .................. B21B 15/00; B21D 39/03; B23P 23/04; B23P 25/00
[52] U.S. Cl. .................. 29/33 K; 29/779; 29/788; 264/46.5
[58] Field of Search .................. 29/460, 418, 155 R, 29/779, 463, 781, 163.5 R, 445, 788, 509, 514, 33 A-33 T; 160/232, 235, 236; 264/46.5, 46.4

[56] References Cited

U.S. PATENT DOCUMENTS

| | | | |
|---|---|---|---|
| 1,352,656 | 9/1920 | Cahill | 160/235 X |
| 3,004,324 | 10/1961 | Macomber | 29/460 X |
| 3,511,301 | 5/1970 | Graham et al. | 160/232 UX |
| 3,547,603 | 12/1970 | Bragman | 29/418 |
| 3,929,949 | 12/1975 | Day et al. | 264/46.4 |
| 3,968,561 | 7/1976 | Oakes et al. | 29/460 |
| 4,162,571 | 7/1979 | Horvay | 29/460 |

FOREIGN PATENT DOCUMENTS

| | | |
|---|---|---|
| 1926417 | 11/1965 | Fed. Rep. of Germany . |
| 1534789 | 8/1969 | Fed. Rep. of Germany . |
| 7143202 | 2/1972 | Fed. Rep. of Germany . |
| 2229079 | 5/1973 | Fed. Rep. of Germany . |
| 2348346 | 4/1975 | Fed. Rep. of Germany . |
| 2735899 | 8/1977 | Fed. Rep. of Germany . |
| 2823732 | 10/1979 | Fed. Rep. of Germany . |
| 1128688 | 1/1957 | France . |
| 2177642 | 11/1973 | France . |
| 2297987 | 8/1976 | France . |
| 642228 | 7/1962 | Italy . |

Primary Examiner—Charlie T. Moon
Attorney, Agent, or Firm—Fitzpatrick, Cella, Harper & Scinto

[57] ABSTRACT

A shutter link (1) for a multi-link overhead shutter or roller blind comprises two sheet metal sheets (7, 8) formed with a cavity (3) between them. The cavity is filled with a heat insulative compound (4) and hinge formations (5, 6) are provided along the longitudinal side of the sheets. Slots (9) are formed along the length of each shutter link on one wide side thereof. The slots are bridged by narrow webs (11) defined by slot interruptions and flanges are provided along the slots on their side facing the cavity with notches (15) formed adjacent to the bending lines and extending parallel to the slots.

13 Claims, 21 Drawing Figures

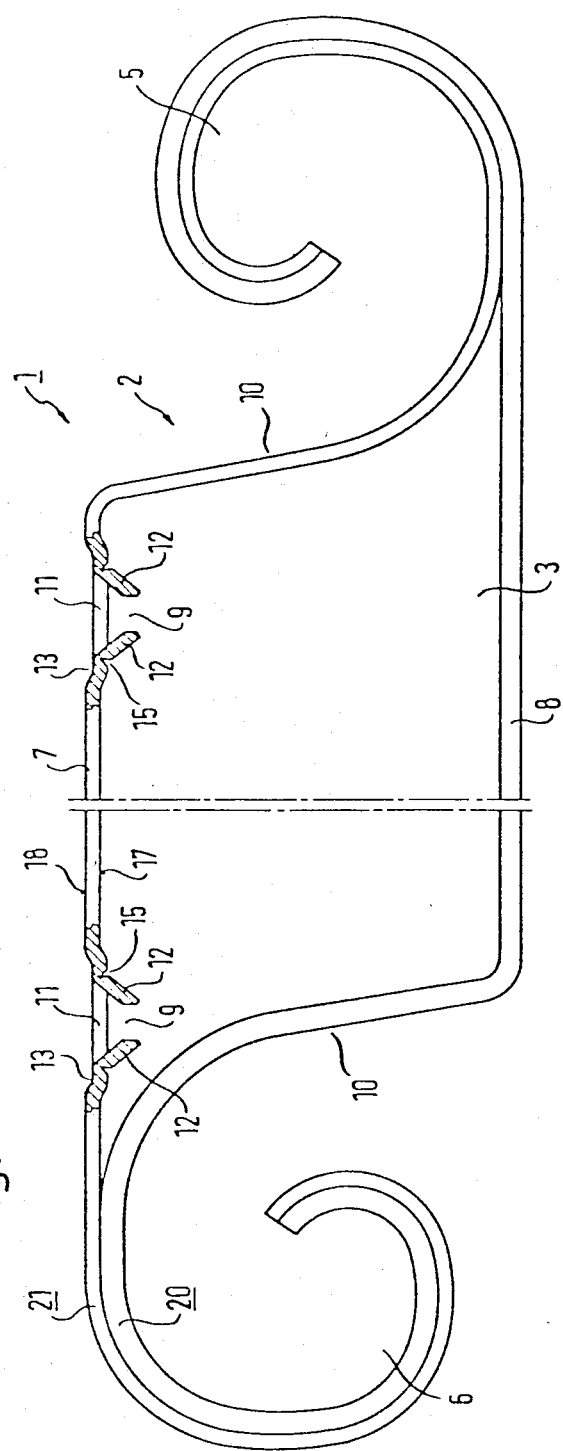
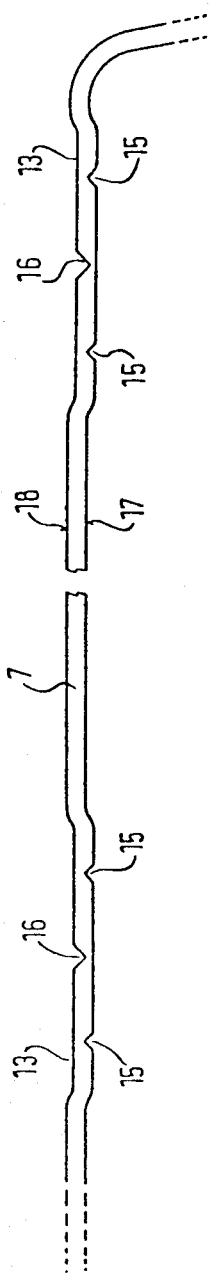
Fig.1
Fig.2

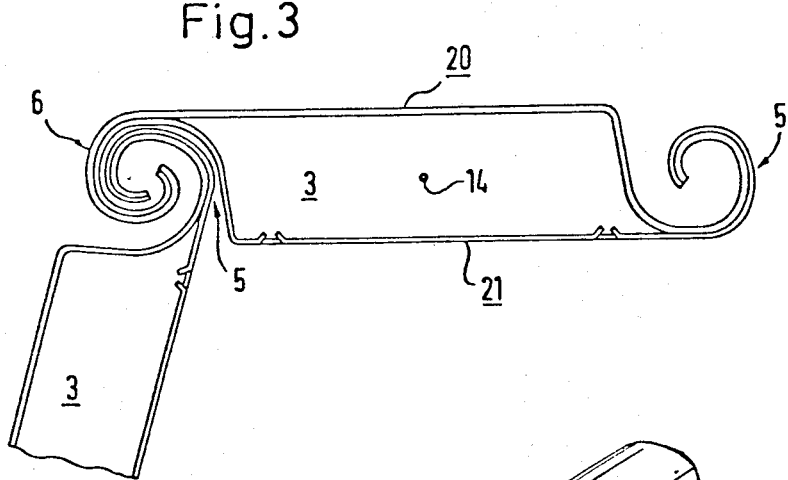
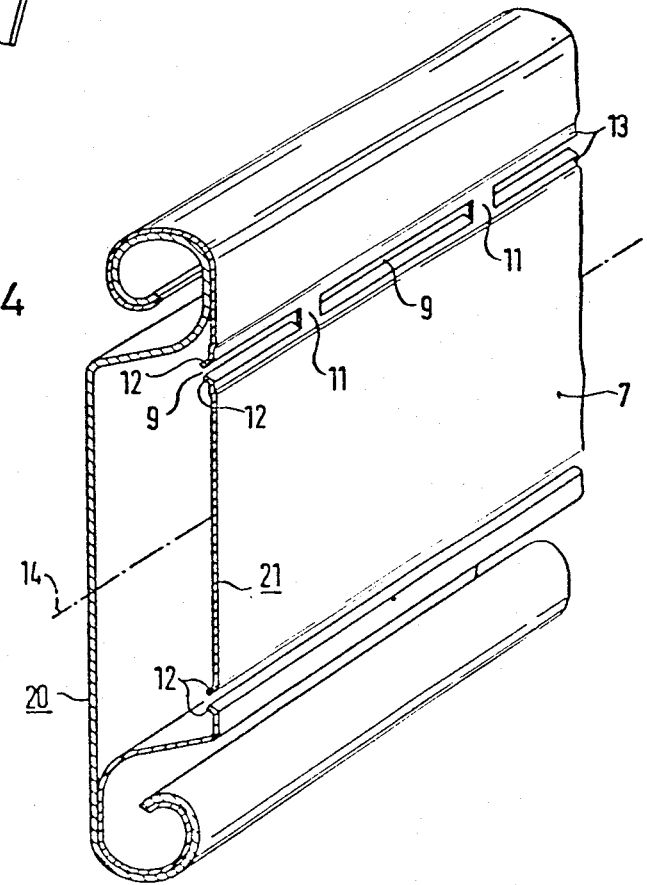

DEVICE FOR MANUFACTURING A SHUTTER LINK FOR A MULTI-LINK OVERHEAD SHUTTER OR ROLLER BLIND

CROSS REFERENCE TO RELATED APPLICATIONS

This is a division of application Ser. No. 308,552 filed Oct. 2, 1981 now U.S. Pat. No. 4,470,444. This application also contains subject matter related to subject in U.S. application Ser. No. 308,551 filed Oct. 2, 1981, now U.S. Pat. No. 4,416,047.

BACKGROUND OF THE INVENTION

1. Field of the Invention

The invention relates to a shutter link for a multi-link overhead shutter or roller blind comprising a hollow section formed by two sheet-metal shells, the cavity of said hollow profile being filled with a heat-insulating compound, said link being provided with hinge elements on the longitudinal edges of the hollow profile, said link being provided with two slots adjacent to the two hinge elements and extending the length of the link, said slots being defined by flanges which are bent inwardly towards the cavity.

2. Description of the Prior Art

There has been known a shutter link of the kind named in German Pat. No. DE-OS 27 35 899. In this known shutter link, the two sheet-metal shells are provided with bent portions on their longitudinal edges which comprise the hinge elements. In the vicinity of the bent portions, there is provided, between the two sheet-metal shells, a slot serving to exclude the formation of a cold-transmitting bridge. The slot is bridged by a diaphragm made of a plastic material which has a low thermal conductivity. The two sheet-metal shells are held together by the heat-insulating foam material extending rearwardly of said bent portions.

While the German Pat. No. DE-OS 27 35 899 does not disclose the manner in which the known shutter link is to be manufactured, it is apparent that the operations of assembling the two sheet-metal shells, of providing the hinge elements and of applying the plastic diaphragm require the expenditure of labor and time and that such operations are not adapted to provide a continuous manufacturing method.

SUMMARY OF THE INVENTION

It is the object of the invention to construct a shutter link of the kind described above in such a manner that it is adapted to be manufactured by means of a continuous automatic manufacturing method.

Said object is attained, according to the invention, by the following features:
(a) the slots are provided on a wide side of the shutter link,
(b) the slots are bridged by narrow webs,
(c) the slots are defined towards the cavity by flanges bent inwardly towards the cavity and converging to form a U-shape, said flanges being provided, on the cavity side, with notches extending parallel to the slot and being disposed adjacent to the base of the bent flanges.

The feature (a) makes it possible to form the slots by means of cutting rolls while the shutter link is supported on its opposite side against the pressure of the slotting rolls by bearing in a simple manner, for example, against a bottom strip without it being necessary to have the shutter link carry with it any special holding means. This is not possible if the slots are provided on the longitudinal edges having the hinge elements formed therein as is the case with the known shutter link.

Feature (b) makes it possible to avoid upward bending of the portion of the respective sheet-metal shell extending between the slots as a result of the deforming pressure applied by the slotting rolls; in addition, this part cannot be separated from the heat-insulating compound if the adhesive power should be reduced.

Feature (c) also assists in the formation of the slots by non-cutting forming by means of slotting rolls which are particularly adapted to be employed in a continuous automatic manufacturing process.

During manufacture of the shutter link of the invention the sheet-metal shell to be provided with the slots may be provided, in addition to the two notches located on the inner side of the cavity, with an additional notch extending centrally between the said notches on the side facing away from the cavity. This additional notch facilitates the operation of forming the slot by means of the slotting rolls.

In a preferred embodiment of the method of manufacturing the shutter links of the invention, provisions are made to have withdrawn from a supply structure two metallic strips which are wound onto strip coils, said strips being transformed into the metallic hollow section by means of a two-window roll forming machine. In this roll forming machine, one of the strips is provided with the beads having the notches formed therein.

In another roll forming machine, the lower surfaces of the pre-profiled strips are forced together by pressure rolls, and their upper surfaces are kept apart by means of a spreading nose or a spreading roll. Disposed in the vicinity of this spreading tool there is disposed the discharge nozzle of a machine serving to introduce, between the strips, a thermosetting foamed plastic material, e.g. polyurethane. This foamed plastic material represents the heat-insulating material. After the introduction of this foamed plastic, the metallic strips are forced together at their upper side in the roll forming machine and attached together, for example, by a suitable bending operation.

In order to avoid any deformation or twisting of the metallic strips joined to form a hollow section or to compensate for such deformation or twisting, the closed metallic strips are passed through straightening means before being transferred to thermosetting means, where thermosetting of the plastic material is effected.

At the end of the curing section, there is provided a length measuring device controlling an automatic cutting-to-length machine. The automatic cutting-to-length machine is provided with a flying saw permitting the moving metallic strip to be cut in such a way as to produce separate metallic hollow profiles having the desired length. In order to prevent jamming within the sawing machine, the individual sections sawn off the strip are withdrawn from the automatic cutting-to-length machine at an increased speed.

In order to assemble a roller blind body, it is necessary to slidingly engage the hinge elements of the individual cut-to-length metallic hollow profiles. For this purpose, there is provided, according to the invention, an automated method. In accordance with this method, a metallic hollow profile is gripped at both ends by means of lifting tongs and lowered by an amount corresponding to the width of the metallic hollow profile. In this lower position, it is then gripped by holding tongs and held in position. After the holding tongs have been operated, the lifting tongs are again moved into their upper position so as again to be ready for operation. Then the next metallic hollow section has its lower hinge element slid into the upper hinge element of the preceding metallic hollow section by means of suitable drive rolls. Following this, the metallic hollow section which has arrived last is gripped by the lifting tongs whereupon this cycle can be executed again.

In accordance with another embodiment of the method of the invention, the metallic hollow sections, after having been slid into engagement, are transferred to a milling unit by means of a transverse conveyor. In this milling unit, slots are cut into the heat-insulating material filling the cavity at the end surfaces of the metallic hollow sections so as to permit end pieces having mounting lugs to be secured in these slots. The forcing-on of these end pieces is effected in a subsequent method step. After forcing-on the end pieces, the individual shutter links which have already been into sliding engagement for the purpose of forming a roller blind are complete. Thereafter, the interlocked shutter links are coiled to form a bale. At the same time a web of paper is inserted between the individual layers formed by the shutter links in order to prevent the shutter links from being marred by scratching. This web of paper is withdrawn from a paper supply roll.

The device employed to perform the manufacturing method of the invention, as far as it is has not already been dealt with in the description of the manufacturing method, will be described in connection with the various embodiments.

BRIEF DESCRIPTION OF THE DRAWINGS

Now the invention will be described and explained, reference being taken to preferred embodiments shown in the figures.

There is shown in

FIG. 1 a cross section of a shutter link according to the invention;

FIG. 2 a wall of the shutter link provided with the notches and beads before having the slots formed therein;

FIG. 3 the lower and upper sides of two shutter links of the invention inserted into one another for the purpose of forming a hinge;

FIG. 4 various embodiments of the slots provided according to the invention;

DETAILED DESCRIPTION OF THE PREFERRED EMBODIMENTS

Figure 5:
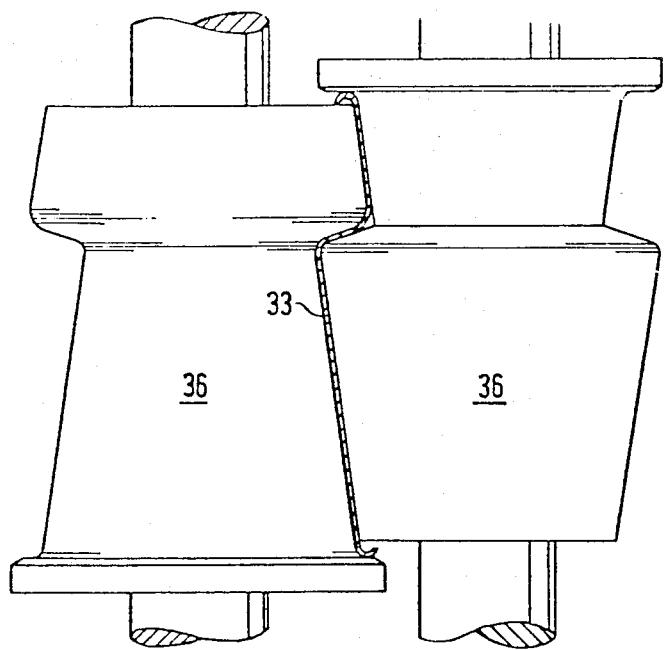
FIGS. 5 and 6 metallic strips which are pre-profiled between the rolls of a roll forming machine.

FIG. 1 shows a cross section of a shutter link 1 according to the invention. It consists of a metallic hollow section formed by two leaves 20, 21 which are bent so as to be in mutual engagement. These leaves 20, 21 are of different thickness. The leaf 20 which forms the outer shell of the profiled body has the larger thickness since it is required to provide the necessary stability and tensile strength of the shutter link. The thinner leaf 21 forms the cavity wall 7 located on the inner side of the blind. There are formed, in this cavity wall 7, beads 13 within which the slots 9 extend. The slots 9 are defined by two flanges 12 bent inwardly towards the cavity 3. The bent edge of the flanges 12 extends along the notches 15. The slots 9 are provided in the vicinity of the narrow sides 10 of the cavity so that a portion of the cavity wall 7 which is as large as possible is disposed in an isolated manner. The cavity 3 of the shutter link is filled with a heat-insulating compound.

FIG. 2 shows that, for the purpose of forming the slots 9, two pairs of notches 15 are formed in the surface 17 of wall 7 facing the cavity 3. On the opposite surface 18 of the cavity wall 7, a notch 16 of greater depth is provided centrally between the two notches 15 of each pair. All three notches 15, 16 are located within a bead 13 which projects towards cavity 3. Upon a tool being forced into notch 16, notch 16 is torn to form a slot 9 as shown in FIG. 1.

On their longitudinal sides, the leaves 20, 21 are bent together to form claws so that they constitute hinge elements 5, 6. FIG. 3 shows the manner in which two hinge elements of two shutter links are mutually articulated.

FIG. 4 shows a perspective representation of a shutter link according to the invention. In the upper part there is shown an embodiment in which the slots 9 are bridged by separate narrow webs 11. These narrow webs provide a strong mechanical connection between the cavity wall 7 facing the space inside the blind and the hinge elements. It will further be seen that the slots 9 are located within a bead 13. The slots 9 are defined by flanges 12 which are bent inwardly towards cavity 3. In the lower part there is shown that the slot 9 may also be continuous.

Figure 6:
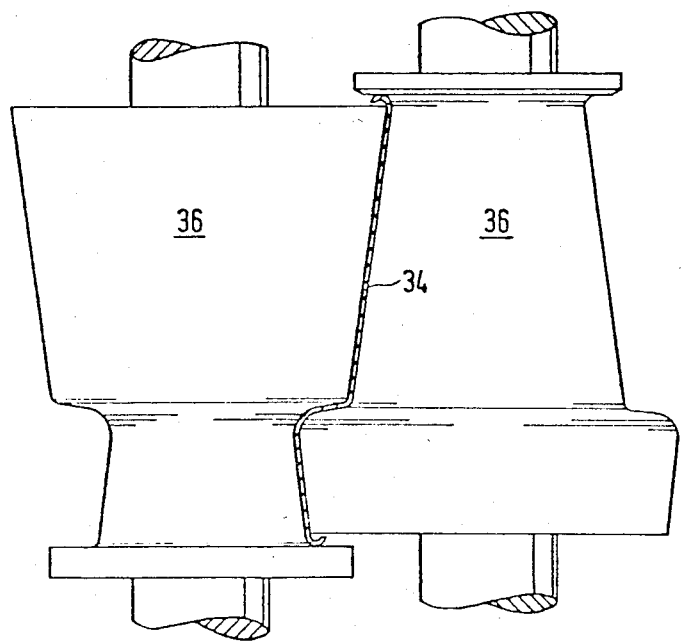
Figure 7:
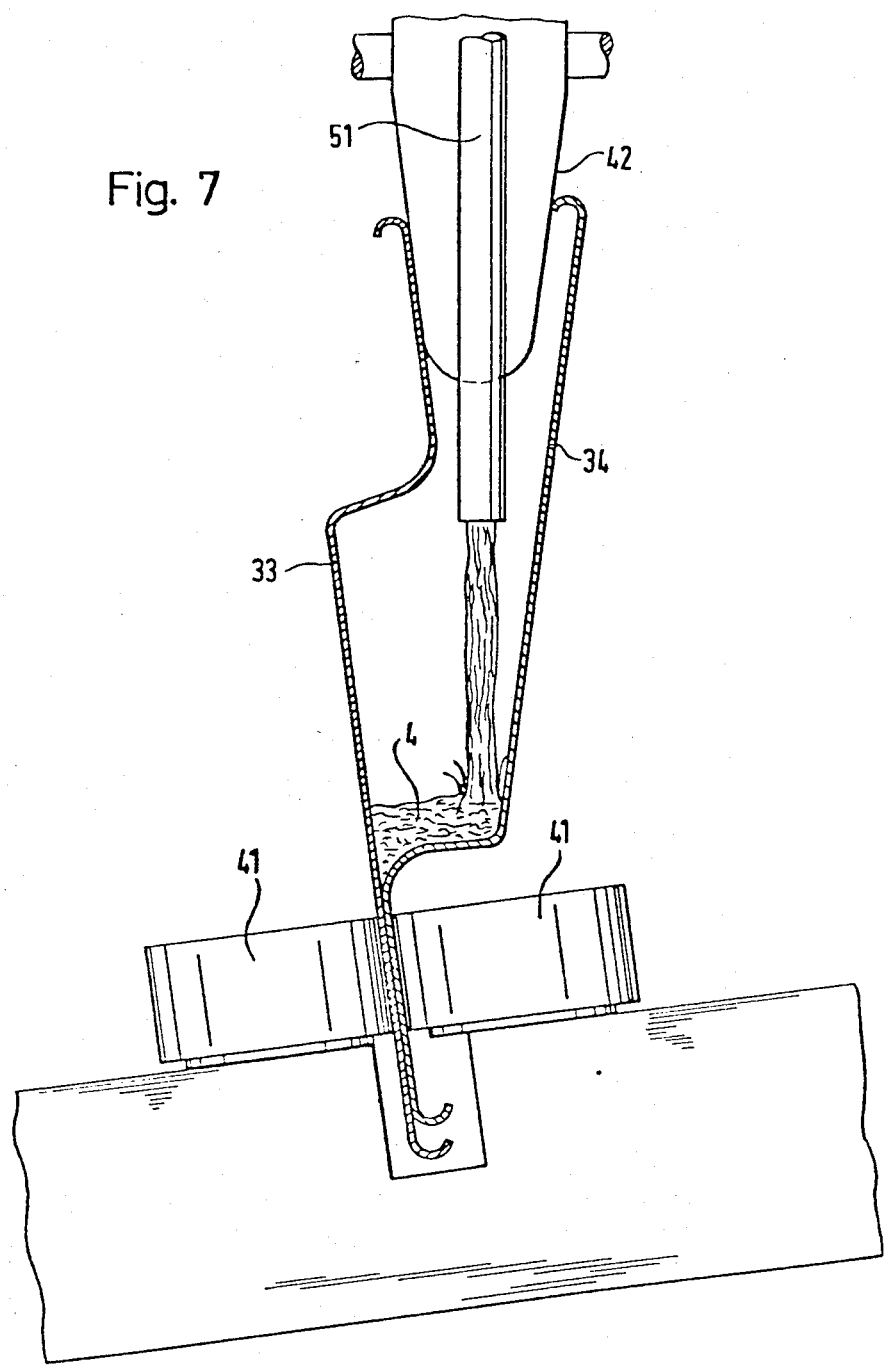
FIG. 7 the introduction of a plastic foam compound between the pre-profiled strips.
Figure 8:
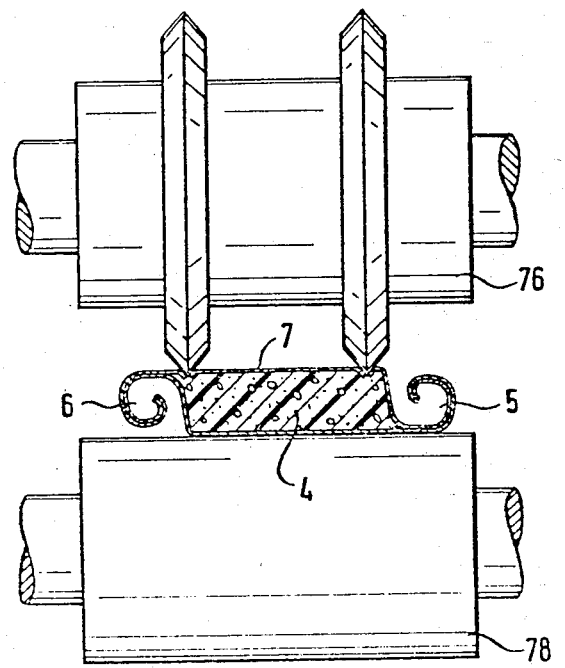
FIG. 8 the operation of forming of the slots provided in accordance with the invention.
Figure 9:
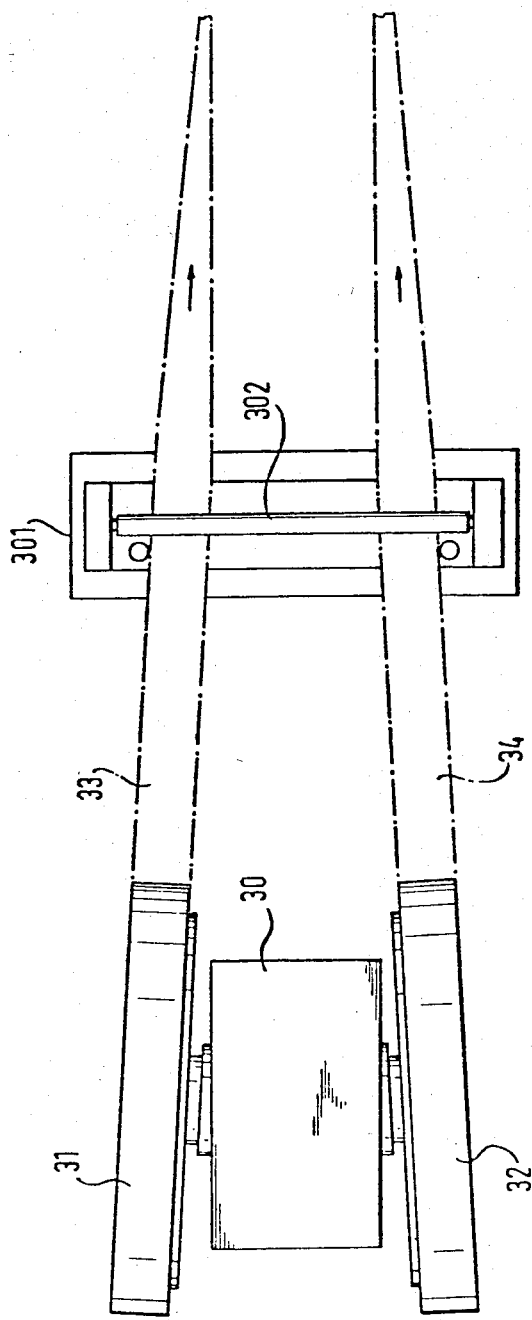
FIGS. 9 and 10 the feeding unit of a manufacturing device suitable for the performance of a continuous manufacturing process.
Figure 10:
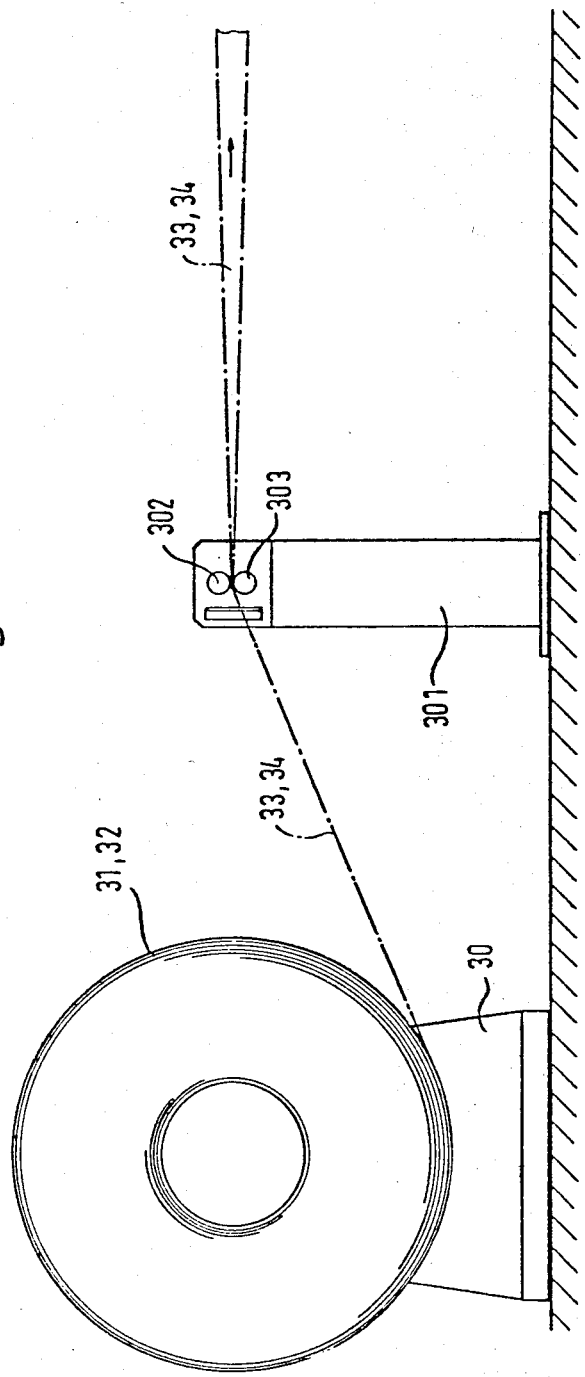
Figure 11:
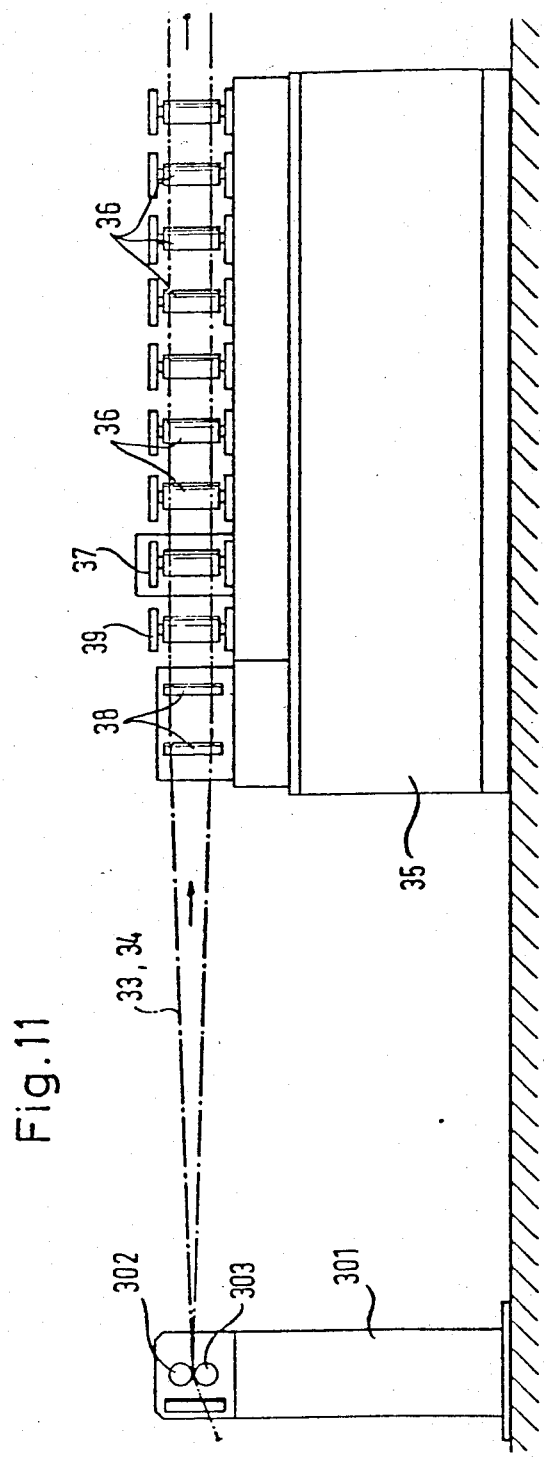
FIGS. 11 and 12 a first roll forming machine for pre-profiling the metallic strips.
Figure 12:
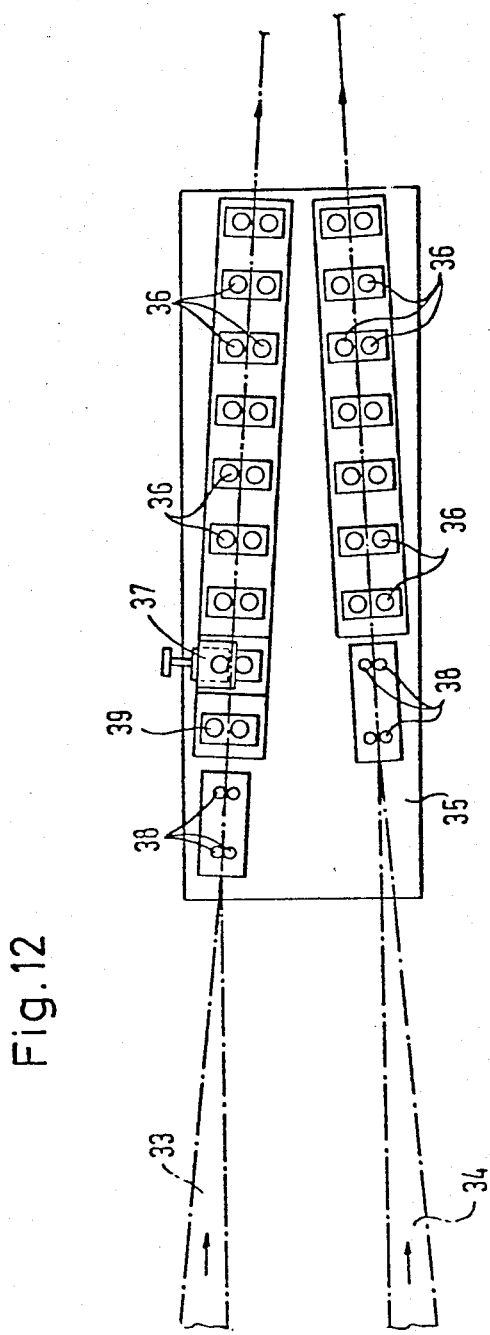
Figure 13:
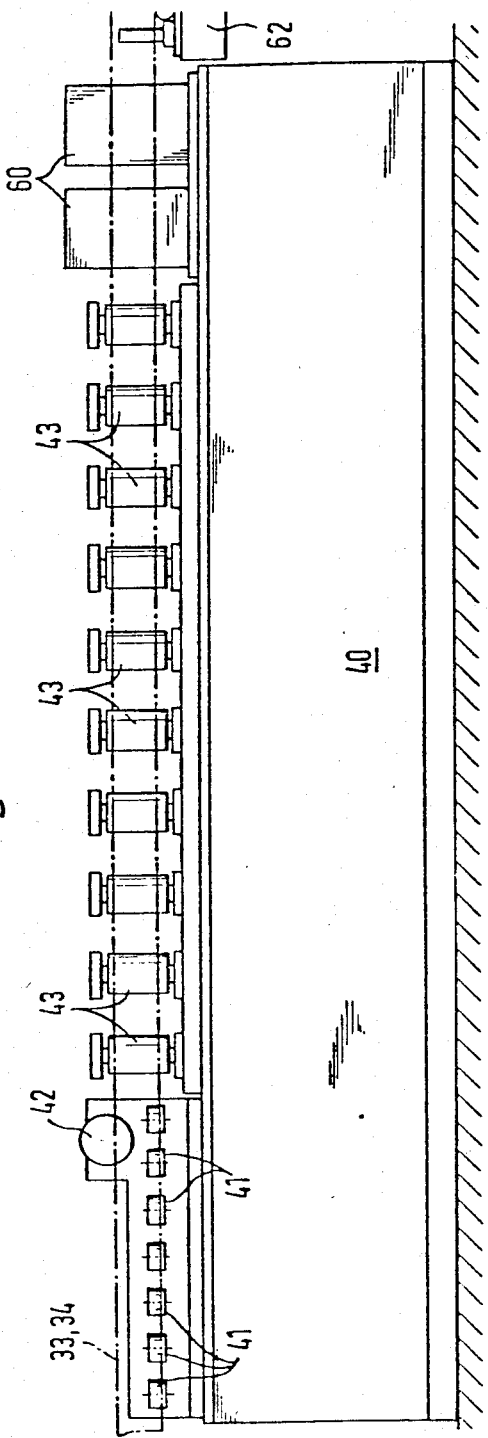
FIGS. 13 and 14 a device which is adapted to spread the upper sides of the metallic strips and to introduce a foamed plastic material as well as a second roll forming machine.
Figure 14:
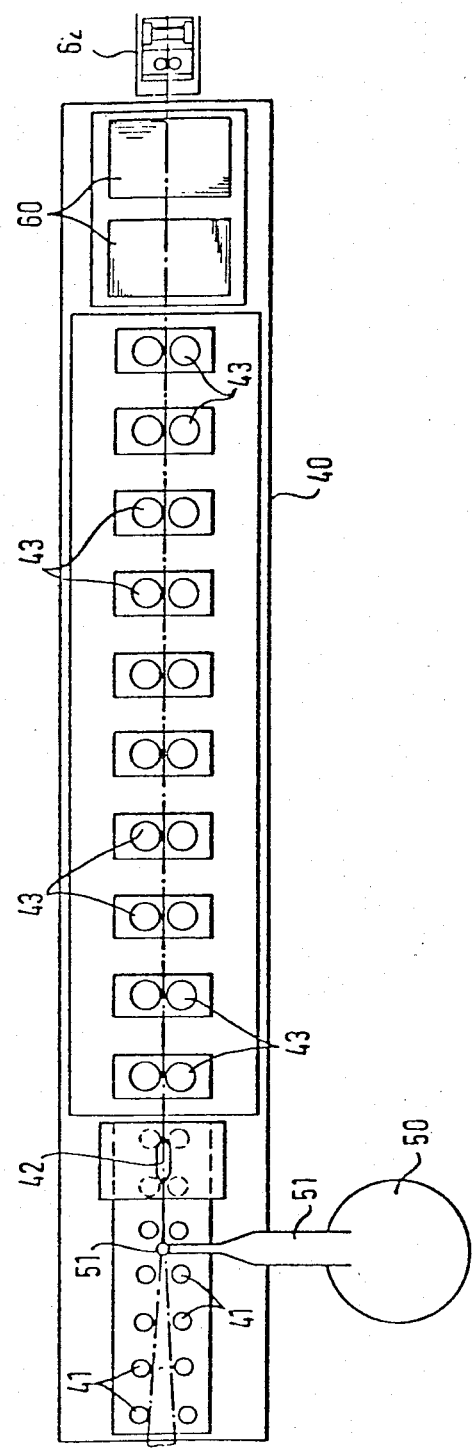
Figure 15:
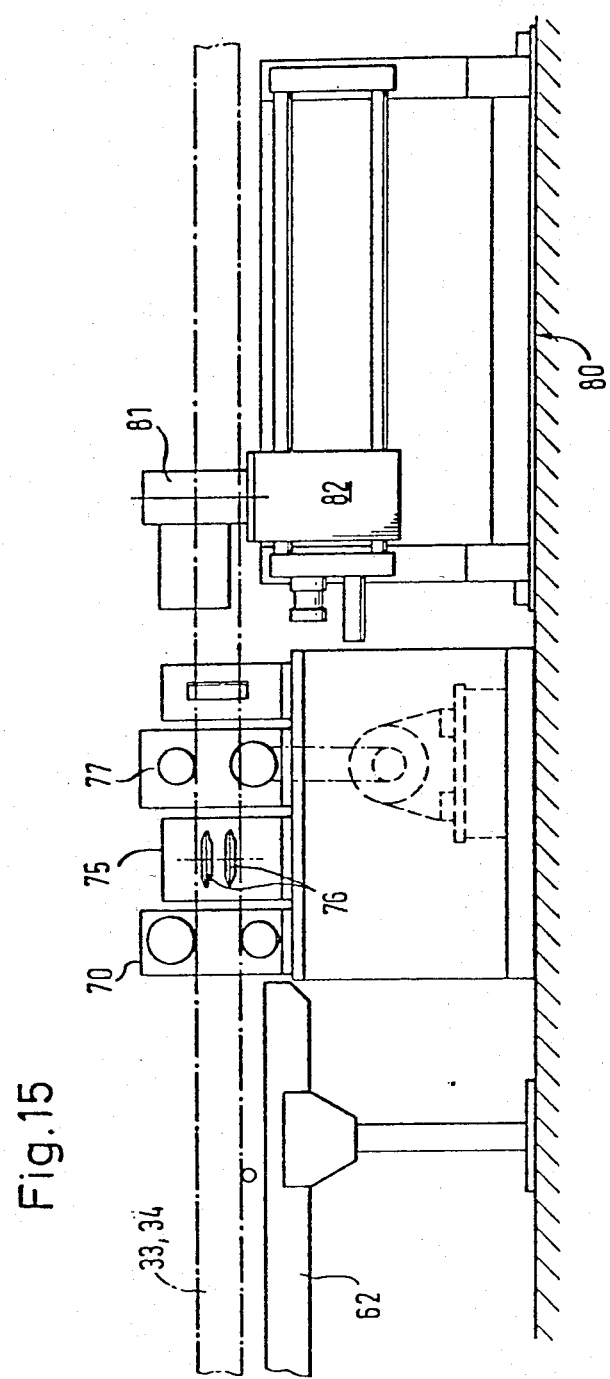
FIGS. 15 and 16 a length measuring unit, a device for forming the slots, a driving unit and an automatic cutting-to-length machine disposed downstream thereof.
Figure 16:
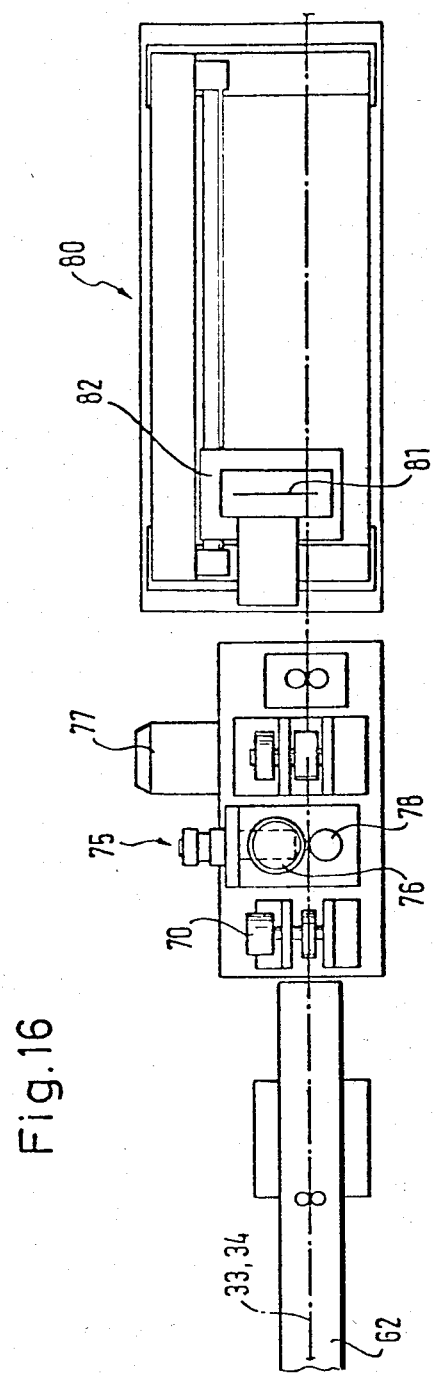
Figure 17:
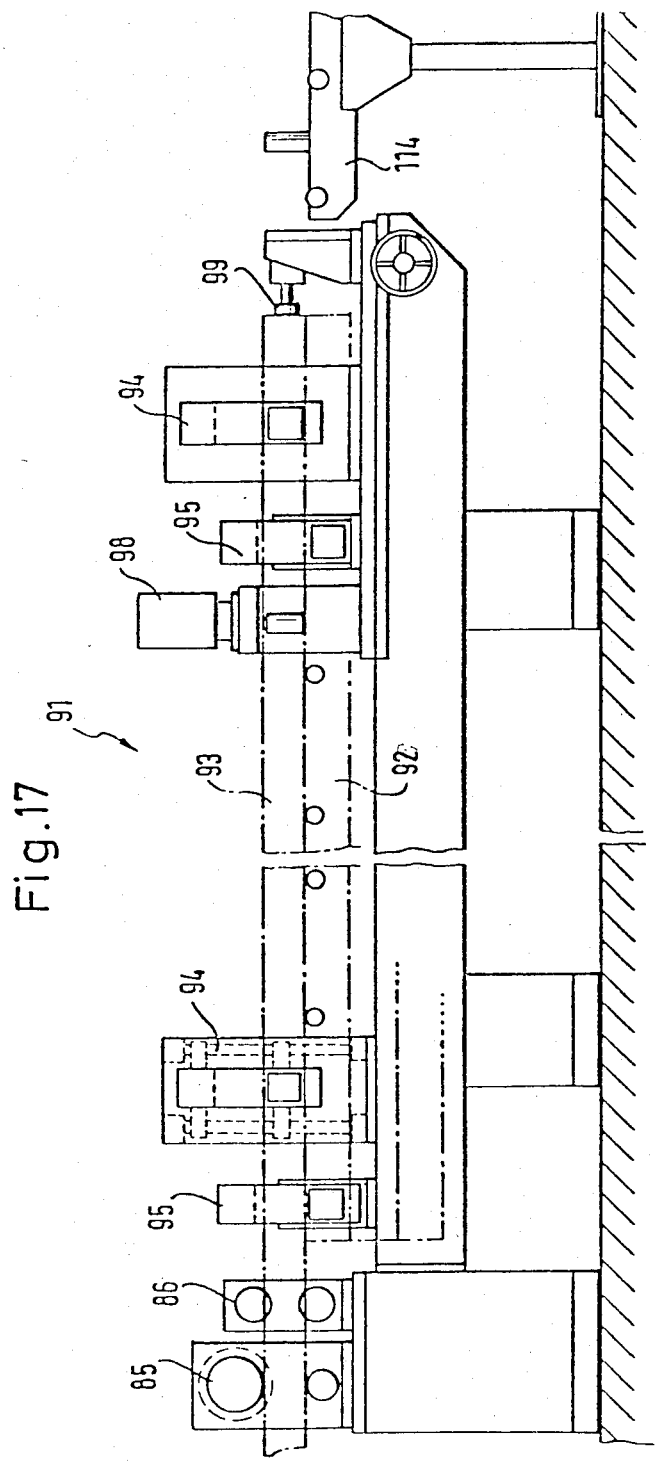
FIGS. 17 and 18 a device for automatic interlocking of the individual metallic hollow sections.
Figure 18:
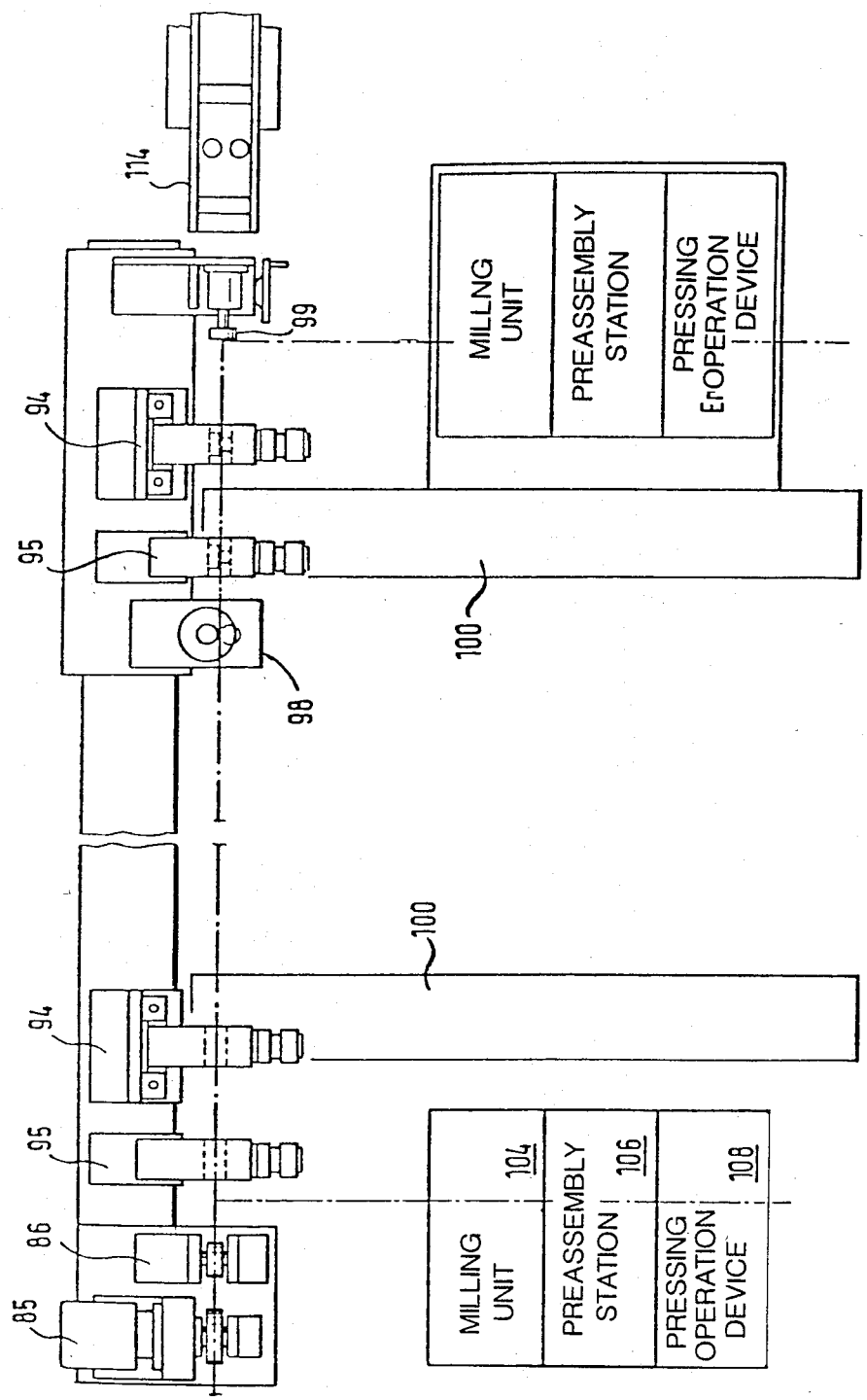
Figure 19:
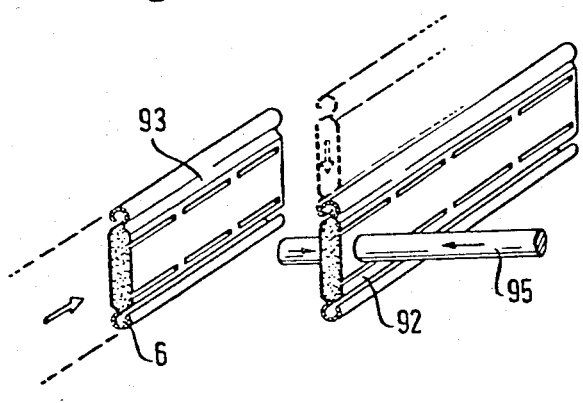
FIG. 19 the operation of interlocking the metallic hollow sections.
Figure 21:
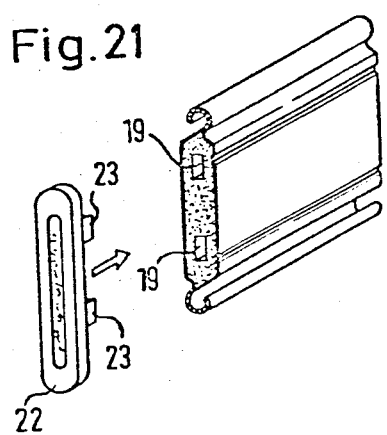
FIG. 21 the forcing-on of the end pieces onto a metallic hollow section.

For the purpose of manufacturing a shutter link according to the invention in a continuous process, metallic strips 33, 34 are withdrawn from a feeding unit 30 supporting two metallic strip coils 31, 32. This feeding unit is shown in FIGS. 10 and 11. From the feeding unit, the metallic strips 33, 34 are withdrawn via rolls 302, 303 of a roll stand 301. The strips are rotated through 90° and driven by means of drive rolls 38 disposed at the entrance of a two-window roll forming machine 35. The thinner metallic strip 33 passes through a bead forming station in which it is provided with a continuous bead by means of suitably shaped rolls 39. Disposed downstream of the bead forming station is a notch forming station in which the metallic strip 33 is provided with the notches 15, 16 shown in FIG. 2. The notches are press-formed by means of rolls 37 provided with cutting edges. Between additional rolls 36, the metallic strips 33, 34 are then pre-profiled. This is shown in FIGS. 5 and 6. Then the metallic strips are forwarded to a second roll forming machine 40 which is shown in greater detail in FIGS. 13 and 14. At the entrance of this second roll forming machine 40 there are disposed pressure rolls 41 between which the lower sides of the pre-profiled strips 33, 34 are forced together. This is shown in greater detail in FIG. 7. The second roll forming machine 40 is further provided with a spreading roll 42 by means of which the upper sides of the pre-profiled strips 33, 34 are kept in a spread-apart condition. This makes it possible, by means of a discharge nozzle 51 of a polyurethane foaming machine extending between the strips 33, 34, to introduce liquid polyurethane as a heat-insulating material 4. Disposed downstream of the station serving to introduce the liquid polyurethane are closing rolls 43 by means of which the upper sides of the pre-profiled strips 33, 34 are closed, and by means of which the upper sides and the lower sides of these strips are joined by bending and formed with claw-shaped hinge elements 5, 6 so as to be fastened together. Disposed at the end of the second roll forming machine 40 is a profile straightening device 60 serving to remove and compensating for any deformation present in the profiled sections formed by the strips 33, 34. From the second roll forming machine the strips, after having been closed to form a hollow section, are forwarded to a curing section 62. This curing section 62 is diagrammatically shown in the left part of FIGS. 15 and 16. From the curing section, the continuous hollow section formed by the metallic strips 33, 34 is forwarded into a length measuring unit 70. This length measuring unit serves to control an automatic cutting-to-length machine 80 by means of which the continuous section is divided into individual pieces by a sawing operation. The length measuring unit is provided with a spring-loaded measuring wheel rolling in contact with the section as well as with length and piece counters. From the length measuring unit the continuous section is then forwarded to a slot forming station 75 in which slotting rolls 76 serve to open the notches 16 so as to form slots 9. The operation of press-forming the slots is detailed in FIG. 8. The section is supported by a supporting roll 78 while the slot-forming roll 76 forms the slots 9 by applying pressure. The slot forming roll 76 may be lifted off the cavity wall 7 of the section so that it is possible to provide separate slots having webs 11 located therebetween. Disposed downstream of the slot forming station is a driving unit 77 serving to push the continuous section towards an automatic cutting-to-length machine 80. This automatic cutting-to-length machine 80 serves to subdivide the continuous section during its motion. For this purpose, it is provided with a flying saw 81 mounted on a saw slide 82. Control of this cutting-to-length slide or the flying saw, respectively, is effected by means of the length measuring unit 70. The arrangement of the length measuring unit, the slot forming station, the driving unit and the automatic cutting-to-length machine is shown in FIGS. 15 and 16. The individual profiled bodies, after having been cut, are accelerated and withdrawn from the automatic cutting-to-length machine by means of a driving unit 85 and forwarded, via guide rolls 86, to an assembling unit 91. This assembling unit 91 serves automatically to join the cut-to-length metallic hollow sections. The metallic hollow section 92 which was inserted as the last one is gripped by lifting tongs 94. These lifting tongs 94 are then moved downwardly into a position in which the metallic hollow section 92 has been lowered in relation to its entering position by an amount which exactly corresponds to the width of the section. In this lower position the metallic hollow section 92 is then gripped by holding tongs 95. By means of driving stand 85 the next metallic hollow section 93 is now introduced into the assembling unit. During this operation, this metallic hollow section 93 has its lower hinge element 6 inserted into the upper hinge element 5 of the metallic hollow section 92 which was introduced first. The excess kinetic energy of the metallic hollow section 93 is dissipated by the damping action of a hinged stop 99 and thus rendered ineffective. After its insertion the metallic hollow section 93 is moved by means of lifting tongs 94 into a lower position in which the metallic hollow section 92 had been before. Subsequently, lifting tongs 94 are again moved into their upper position while lifting tongs 95 are holding the metallic hollow section 93. Now it is possible to insert another profiled section. The arrangement comprising the driving stand 85, the guide rolls 86 and the assembling unit 91 is shown in greater detail in FIGS. 17 and 18. FIG. 19 shows in more detail the manner in which the metallic hollow sections 92 and 93 are brought into engagement. The lifting tongs 95 are diagrammatically represented by two rods which are forced against the section 92. If it is intended not to engage the individual sections with one another but to pack them singly, the lifting and holding tongs are not operated, and the stop 99 is swung aside so that the individual sections will be forwarded from the driving roll 98 onto the roller conveyor 114.

Figure 20:
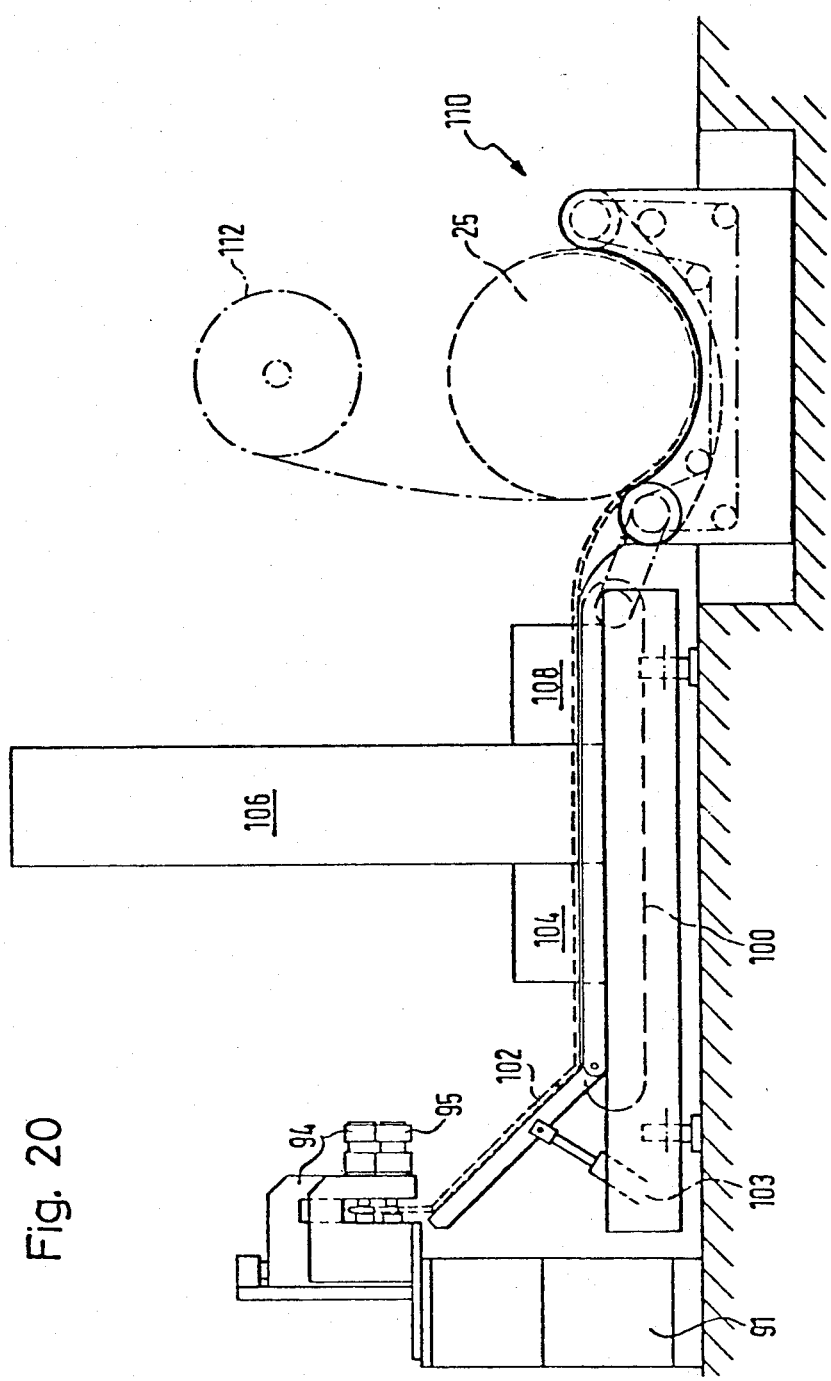
FIG. 20 the transfer of the interlocked metallic hollow sections to a milling unit and a device for forcing-on the end pieces as well as a coiling device.

The remaining operating cycle is illustrated in FIG. 20. There can be seen in the left-hand part of FIG. 20 the assembling unit 91 comprising the holding tongs 95 and the lifting tongs 94 which are movable between two different positions. The profiled sections engaged with one another slide downwardly over a pivotable inclined plane 102 to enter a transverse conveyor 100. The inclined plane may be operated by means of a pneumatic cylinder 103. The transverse conveyor 100 may be operated in a step-by-step manner. It serves to forward the interengaged profiled sections one by one into a milling unit 104. In this milling unit, every second profiled section is provided, by a milling operation, with a slot cut into it from above and from below, respectively. Thereafter the transverse conveyor 100 forwards the individual profiled sections towards a preassembly station 106 in which an end piece 22 removed from a magazine is slid onto each end of the section via a guide rail. Then these end pieces 22 are fixed by a pressing operation performed in another device 108 so that their mounting lugs 23 engage the slots 19. After this assembly of the end pieces, the individual metallic hollow sections have reached the stage of completed shutter links. These shutter links have already been interengaged to form a roller blind so that no further operations are required. In a coiling station 110, the interconnected shutter links are coiled to form a bale 25. A paper web is inserted between the individual layers of the bale 25, this web being withdrawn from a supply roll 112. After the last profiled section of a shutter blind has been assembled and has left the vicinity of the mounting tongs, and if the next shutter blind to be made comprises shutter links of different length, the unit comprising the holding tongs, the lifting tongs and the damping stop is adjusted to suit the new predetermined rod length. This rod length is simultaneously inputted into the length measuring device and thus also into the automatic cutting-to-length machine. At the same time, the number of cycles of the transverse conveyor 100 and the number of cycles of the milling unit and of the endpiece mounting unit are reduced so that a space is provided between the leaving shutter blind and the shutter blind which is being newly introduced. As soon as the leaving shutter blind has been fitted with its end pieces, also the milling unit and the end piece mounting unit are adjusted to suit the new length of the shutter blind.

We claim:

1. A device for manufacturing, in a continuous manner, shutter links for a multilink overhead-shutter or roller blind, said shutter links each comprising a pair of leaves which are bent into mutual engagement along their opposite longitudinal edges and which are shaped to form a cavity between said edges, said cavity being filled with a heat insulating compound, said device comprising a supply stand supporting two metallic strip coils, a first roll forming machine located along a path extending from said supply stand, said roll forming machine being provided with drive and shaping rolls to drive metallic strips from said strip coils and to shape the strips into the shape of the leaves of the shutter link elements and a second roll forming machine also located along said path beyond said first roll forming machine, said second roll forming machine having first pressure rolls adapted to force the shaped strips together along one longitudinal edge thereof, a spreading element positioned to extend between and force apart the other longitudinal edges of said strips, a filling nozzle positioned downstream of said spreading element for injecting a heat insulating compound between said forced apart other edges and into the cavity between the leaves and closing rolls arranged downstream from said filling nozzle to force the shaped strips together along said other longitudinal edge.

2. The device of claim 1 wherein there is provided a slot-forming station having one or a plurality of slot-forming rolls constructed and arranged for the purpose of press-forming slots in said metallic strips.

3. The device of claim 1 wherein there is provided a length measuring unit constructed and arranged for the purpose of measuring the length of the profiled section passed therethrough.

4. The device of claim 3 wherein there is provided an automatic cutting-to-length unit which includes a flying saw comprising a moveable saw slide and a clamping device for the profiled sections, said unit being adapted to be controlled by the length measuring unit.

5. The device of claim 4 wherein there is provided a driving unit adapted to withdraw from the automatic cutting-to-length unit, cutoff metallic hollow sections.

6. The device of claim 5 wherein there is provided an automatic assembling unit adapted to bring into mutual engagement hinge elements of the cut-off metallic hollow sections, the assembling unit being provided with lifting tongs adapted to be slidably moved between two positions and with holding tongs.

7. The device of claim 6, wherein there are provided a pivotable inclined discharge plane and a transverse conveyor adapted to be controlled in a step-by-step manner serving to convey the metallic hollow sections which have been brought into mutual engagement.

8. The device of claim 7, wherein there are provided a milling unit adapted to cut slots into the lateral end faces of the metallic hollow sections and a unit adapted to force end pieces into position.

9. The device of claim 7 wherein there is provided a coiling device adapted to wind up shutter links which have been brought into mutual engagement.

10. The device of claim 9, wherein there is provided a paper supply roll comprising a paper web which is grasped by said coiling device and is inserted between the layers formed by the shutter links.

11. A device according to claim 1 wherein said second roll forming machine further comprises a straightening section adapted to straighten the strips downstream of said closing rolls.

12. A device according to claim 1 and further including a polyurethane foaming machine having its output connected to said filling nozzle.

13. A device according to claim 1 and further including a curing section having guiding and supporting rolls located downstream from said filling nozzle.

* * * * *